(12) United States Patent
Cookson et al.

(10) Patent No.: US 6,387,615 B2
(45) Date of Patent: *May 14, 2002

(54) METHODS AND MATERIALS FOR THE DIAGNOSIS OR PROGNOSIS OF ASTHMA

(75) Inventors: William Osmond Charles Michael Cookson, Oxford; Miriam Fleur Moffatt, Bicester, both of (GB)

(73) Assignee: ISIS Innovation Limited, Oxford (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/058,165

(22) Filed: Apr. 10, 1998

Related U.S. Application Data
(60) Provisional application No. 60/043,856, filed on Apr. 11, 1997.

(51) Int. Cl.$^7$ .................. C12Q 1/68; C12P 19/34; C07H 21/04

(52) U.S. Cl. .................. 435/6; 435/91.2; 536/24.33; 536/24.31

(58) Field of Search .................. 536/24.33, 24.31; 435/6, 91.2

(56) References Cited

U.S. PATENT DOCUMENTS 4,683,202 A * 7/1987 Mullis .................. 435/91
5,468,613 A * 11/1995 Erlich et al. .................. 435/6

OTHER PUBLICATIONS

Lewin. Genes V. Oxford University Press. New York. pp. 1135–1137, 1994.*
Tan et al. Allergy. 54(4): 402–403, Apr. 1999.*
Campbell et al. Eur. Resp. J. 8:552S (supplement), Sep. 1995.*
Campbell et al. Eur. Res. J. 9(23):435s (supplement), Sep. 1996.*
C. Jacob et al., "Heritable major histocompability complex class II–associated differences in production of tumor necrosis factor α: Relevance to genetic predisposition to systemic lupus erythematosus", Proc. Natl. Acad. Sci., vol. 87, pp. 1233–1237, Feb. 1990.
A. Wilson et al., "Effects of a tumor necrosis factor (TNFα) promotor base 167 transition on trancriptional activity". (1994) Br. J. Rheumatol. (33):89.
G. Messer et al., "Polymorphic structure of the tumor necrosis factor (TNF) locus: An NcoI polymorphism in the first intron of the human THF–β gene correlates with a variant amino acid in position 26 and a reduced level of TNF–β production", J. Exp. Med., vol. 173, pp. 209–219, Jan. 1991.
S. Nedospasov et al., "DNA sequence polymorphism at the human tumor necrosis factor (TNF) locus", The Journal of Immunology, vol. 147, No. 3, pp. 1053–1059, Aug. 1, 1991.
I. Udalova et al., "Highly informative typing of the human TNF locus using six adjacent polymorphic markers", Gemonics, vol. 16, pp. 180–186, (1993).

* cited by examiner

Primary Examiner—W. Gary Jones
Assistant Examiner—Juliet C. Einsmann
(74) Attorney, Agent, or Firm—Wenderoth, Lind & Ponack, L.L.P.

(57) ABSTRACT

The present invention is directed to a method for diagnosing an individual as being asthmatic, or of having a predisposition to asthma, and a kit therefor, which method comprises demonstrating in the individual the presence or absence of an unusual variant form of a polynucleotide sequence in the MHC region of chromosome 6p, said unusual variant form being associated with an increased secretion of TNF.

15 Claims, 1 Drawing Sheet

METHODS AND MATERIALS FOR THE DIAGNOSIS OR PROGNOSIS OF ASTHMA

Figure 1:
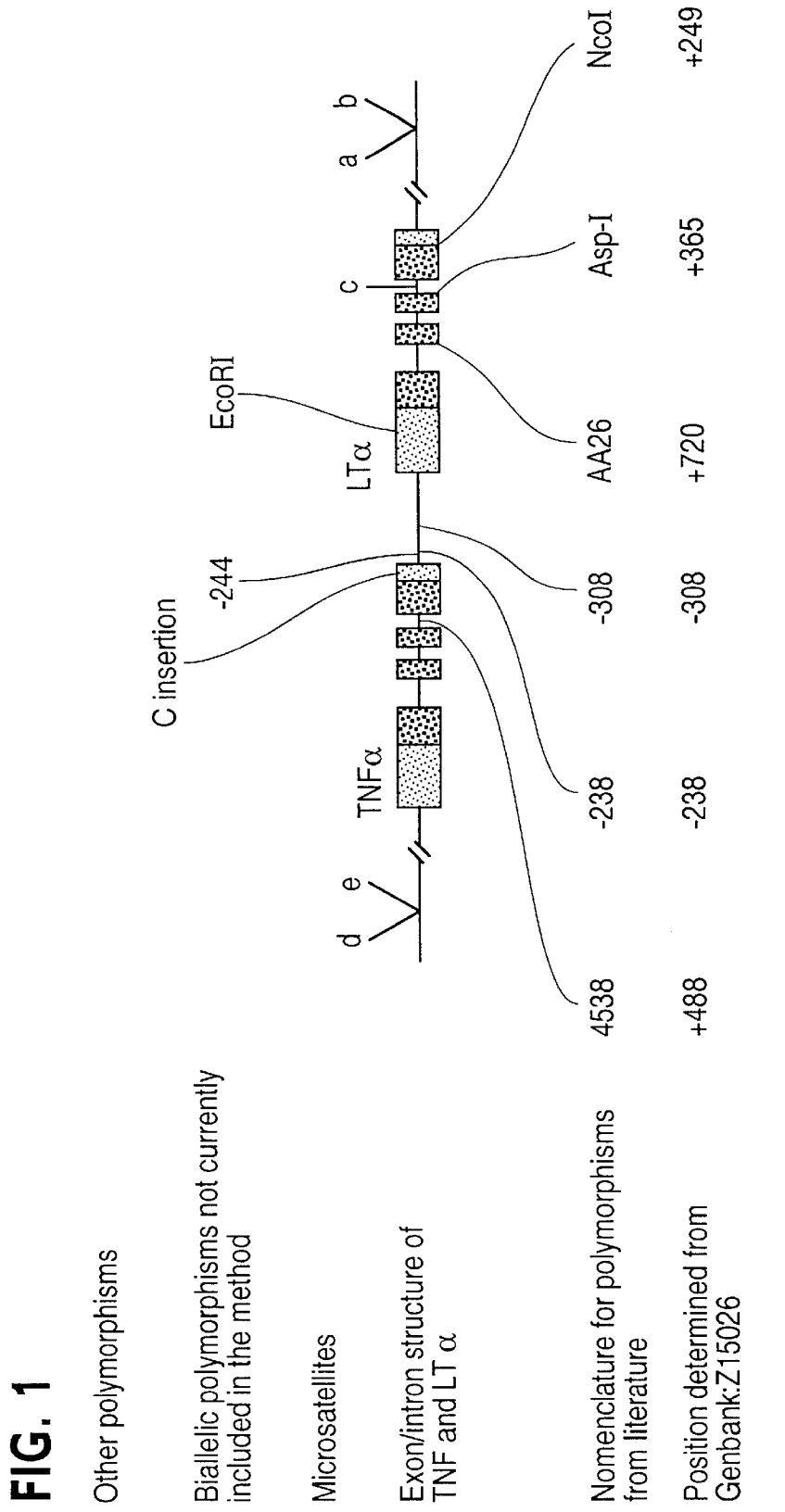

This application claims the benefit of U.S. Provisional Application No. 60/043,856, filed Apr. 11, 1997.

BACKGROUND OF THE INVENTION

1. Field of the Invention

This invention relates to diagnosis of asthma and to materials and methods relating thereto.

2. Description of the Related Art

Asthma is a disease which is becoming more prevalent and is the most common disease of childhood (1). Most asthma in children and young adults is initiated by IgE mediated allergy (atopy) to inhaled allergens such as house dust mite and cat dander However, not all asthmatics are atopic, and most atopic individuals do not have asthma. Thus, factors in addition to atopy are necessary to induce the disease (2,3). Asthma is strongly familial, and is due to the interaction between genetic and environmental factors. The genetic factors are thought to be variants of normal genes ("polymorphisms") which alter their function to predispose to asthma.

Asthma may be identified by recurrent wheeze and intermittent air flow limitation. An asthmatic tendency may be quantified by the measurement of bronchial hyper-responsiveness in which an individual's dose-response curve to a broncho-constrictor such as histamine or methacholine is constructed. The curve is commonly summarised by the dose which results in a 20% fall in air flow (PD20) or the slope of the curve between the initial air flow measurement and the last dose given (slope).

In the atopic response, IgE is produced by B-cells in response to allergen stimulation. These antibodies coat mast cells by binding to the high affinity receptor for IgE (FcεRI). When a multivalent allergen binds to an IgE-coated mast cell, the cross-linking of adjacent IgEs by allergen initiates a series of cellular events leading to the destabilisation of the cell membrane and release of inflammatory mediators. This results in mucosal inflammation, wheezing, coughing, sneezing and nasal blockage.

Atopy can be diagnosed by (i) a positive skin prick test in response to a common allergen; (ii) detecting the presence of specific. serum IgE for allergen; or (iii) by detecting elevation of total serum IgE.

Genetic associations with atopy have been demonstrated. WO 95/05481 discloses that variants of the gene encoding the β-subunit of the high-affinity receptor for IgE (FcεRIβ) are associated with atopy. It teaches a method for diagnosing atopy which is based upon the demonstration of the presence or absence of one of two variants in a specific portion of the DNA sequence of the gene encoding FcεRIβ, located near the commencement of exon 6 of the FcεRIβ gene on chromosome 11. A further variant has also been found in which the unusual variant sequence is in the coding sequence for the C-terminal cytoplasmic tail of FcεRIβ (11).

The known polymorphisms do not account for all of the genetic factors which predispose to asthma. In particular, asthma is not necessarily an atopic disease. Identification of further genetic polymorphisms linked to asthma will allow the identification of children at risk of asthma before the disease has developed (for example immediately after birth), with the potential for prevention of disease.

Tumour necrosis factor (TNF, also known as TNFα) is a potent proinflammatory cytokine that is found in increased concentration in asthmatic airways (4) and in lavage fluid from asthmatic lungs (5). Increased secretion of TNF by peripheral blood lymphocytes or monocytes has also been established in association with the HLA-DRB1*03 genotype (8). The TNF locus is located within the major histocompatibility complex (MHC) between the MHC class III genes and HLA-B. Located downstream of the TNF gene and in tandem arrangement with it is the lymphotoxin α gene (LTα, which was originally designated TNFβ). Unlike the highly polymorphic class I and class II HLA genes, the coding portions of the TNFα and LTα genes only show a very low degree of polymorphism.

The TNFα and LTα loci have been investigated in association with autoimmune diseases such as systemic lupus erythematosus (SLE). It has been suggested that an increased level of TNF secretion is associated with allele 1 of a NcoI polymorphism in the LTα gene (9) and with allele 2 of a TNF promoter variant at position −308 (10). These polymorphisms are known as LTα NcoI*1 and TNF −308*2 respectively. However, there has been some doubt about the significance of these polymorphisms in particular, it has been suggested that the TNFα −308 polymorphism is not relevant to TNFα gene regulation (15, 16).

Several polymorphic microsatellite sequences within the human TNF/LT locus have also been mapped and characterised (12) and used in a cell typing study (13).

It has now been discovered that, surprisingly, unusual genetic variants in or linked to the TNFα gene are predictive of asthma Furthermore, it has been found that the unusual variants are predictive of bronchodilator and inhaled or oral steroid usage in asthmatic individuals. The variants are therefore useful to predict the clinical course of disease (e.g., severe as opposed to mild) or the response to particular treatments, as well as in a diagnostic tool. This information will be of use in relation to both individuals and population, and will be of interest to the insurance industry as well as to the healthcare and pharmaceutical industries.

These unexpected findings make possible new diagnostic and therapeutic strategies.

SUMMARY OF THE INVENTION

The present invention therefore provides a method for diagnosing an individual as being asthmatic, or of having a predisposition to asthma, which method comprises demonstrating in the individual the presence or absence of an unusual variant form of a polynucleotide sequence in the MHC region of chromosome 6p, said unusual variant form associated with an increased secretion of TNF. In particular, the variant may be located in the TNFα/LTα locus, including regulatory regions for the TNFα and LTα genes. FIG. 1 shows a physical map of the human TNFα/LTα, locus and the locations of various polymorphisms using nomenclature as it appears in the literature The variant may be for example allele 1 of the NcoI polymorphism in the LTα gene, or it may be allele 2 of the TNF promoter polymorphism at position −308. Both of these variants have been described in detail previously in references 10 and 14, the contents of which are incorporated herein by reference. The method according to the invention may involve identifying the presence or absence of two or more such variants.

The sequence difference between the two alleles of the TNF −308 polymorphism is a single base change at position −308 relative to the transcription start site of the gene. For allele 1 the nucleotide at position −308 is a guanine "G". For allele 2 the nucleotide at position −308 is an adenine "A".

The sequence difference between the two alleles of the NcoI polymorphism in the LTα gene is a single base change at position +252 relative to the transcription start site. For allele 1 the nucleotide at position +252 is a G which forms part of a restriction site which the NcoI enzyme cuts. For allele 2 the nucleotide at position +252 is an A and the NcoI enzyme does not cut.

Suitable techniques for identifying the presence or absence of the variants are described herein. However, the invention is not limited to these specific methods. Modified versions of these methods, and alternative techniques, will be known to those skilled in the art.

A technique may be employed which uses one or more complementary nucleic acid sequences which are specific for the unusual variant and not for the wild-type. The complementary nucleic acid sequence may simply be used as a probe specific for the unusual variant. Alternatively, one or more suitable complementary nucleic acid sequences may be used as primers in a detection system comprising a polynucleotide amplification technique such as PCR or ARMS. DNA or RNA-based amplification methods may be employed. Thus the amplification may be carried out based on mRNA or cDNA made from mRNA. PCR may be followed by probing the amplification products with a sequence-specific nucleic acid probe capable of annealing to a portion of the amplified polynucleotide sequence which is specific to the unusual variant and not to the wild-type. Alternatively, confirmation of the amplification product may be obtained by probing or sequencing or by restriction digestion of the amplification product if the variant introduces or abolishes a restriction endonuclease site, or by other known methods. If the PCR primers used are specific to the variant, there will only be successful amplification if the variant is present in the test sample. Alternatively the primers used could be non-specific to the variant the amplification serving only to increase sample material for sequencing or for restriction digestion or for subsequent probing with a probe specific to the unusual variant and not to the wild-type.

Suitable specific complementary nucleic acid sequences for use as probes and primers in a detection assay for an unusual variant according to the invention, whether or not involving an amplification step, can be ascertained from the known DNA sequences. The human MHC region has been extensively characterised and sequenced. The sequence for the TNFα/LTα locus is available under database reference z15026.emhum2. The nucleotide sequences for the LTα NcoI*1 and TNF −308*2 alleles are available in the published literature (10, 14) and are incorporated herein by reference.

The method according to the invention includes identifying variants not only by nucleic acid based techniques, but also in the case of coding sequences, by techniques which detect polymorphic forms of an amino acid sequence coded for by the nucleic acid variant. Where analysis is made of the amino acid sequence this may be done by sequencing studies, or by use of a probe which comprises an antibody binding domain which is specific for the unusual polymorphic form of the amino acid sequence. Conveniently, such probes are labelled with a detectable label.

The invention will be useful not only for the diagnosis of individuals, but also for assessing the risk of asthma across populations. Population statistics can provide organisations such as healthcare organisations and insurance companies with valuable information for planning purposes.

The invention as described may be employed together with other methods for diagnosing asthma or a predisposition to asthma. This includes other methods which detect polymorphisms, for example those described in WO 95/05481, WO 97/08338 and Hill et al (11) for diagnosing atopic asthma, or methods which investigate asthma by looking at physiological symtoms.

The invention will also be useful for predicting the clinical course of asthma, both in individuals and across populations, and the method according to the invention may therefore be performed as such. This may be used to identify asthmatic individuals who may respond to treatment directed against TNF or other pro-inflammatory molecules which interact with TNF.

REFERENCES

1. Strachan, D. P., Anderson, H. R., Limb, E. S., O'Neill, A. and Wells, N. (1994) A national survey of asthma prevalence, severity, and treatment in Great Britain. *Arch. Dis. Child*, 70, 174–178.
2. Fraser, R. S., Paré, J. A. P., Fraser, R. G. and Paré, P. D., eds. (1994) Synopsis of Diseases of the Chest. WB Saunders Company, Philadelphia: 635–53.
3. Djukanovic, R., Roche, W. R., Wilson, J. W. Beasley, C. R., Twentyman, O. P., Howarth, R. H. and Holgate S. T. (1990) Mucosal inflammation in asthma. *Am. Rev. Respir. Dis.*, 142, 434–457.
4. Broide, D. H, Lotz, M., Cuomo, A. J., Coburn, D. A., Federman, E. C. and Wasserman, S. I. (1992) Cytokines in symptomatic asthma airways. *J. Allergy Clin. Immunol.* 89, 958–967.
5. Virchow, J-C., Walker, G., Hafner, D., Kortsik, C., Werner, P.; Matthys, H. and Kroegel, C. (1995) T cells and cytokines in bronchoalveolar lavage fluid after segmental allergen provocation in atopic asthma. *Am. J. Respir. Crit. Care. Med.*, 161, 960–968.
6. Dunham, I., Sargent, C. A, Trowsdate, J. and Campbell, R. D. (1987) Molecular mapping of the human major histocompatibility complex by pulsed-field gel electrophoresis. *Proc. Natl. Acad. Sci. USA*, 84, 7237–7241.
7. Nedospasov, S. A., Shakhov, A. N., Turetskaia, R. L., Melt, V. A. and Georgiev, G. P. (1985) [Molecular cloning of human genes coding tumor necrosis factor: tandem arrangement of alpha- and beta-genes in a short segment (6 thousand nucleotide pairs) of human genome]. *Doki. Akad. Nauk. SSSR*, 285, 1487–1490.
8. Jacob, C. O., Fronek, Z., Lewis, G. D., Koo, M., Hansen, J. A, and McDevitt, H. O. (1990) Heritable major histocompatibility complex class II-associated differences in production of tumor necrosis factor: Relevance to genetic predisposition to systemic lupus erythematosus. *Proc. Natl. Acad. Sci. USA* 87, 1233–1237.
9. Messer, G., Spengler, U., Jung, M. C., Honold, G., Blömer, K., Pape, G. R., Riethmüller, G. and Weiss E. H. (1991) Polymorphic Structure of the Tumor Necrosis Factor (TNF) Locus: An NcoI Polymorphism in the First Intron of the Human TNF-Gene Correlates with A Variant Amino Acid in Position 26 and a Reduced level of TNF-Production. *J. Exp. Med.*, 173, 209–219.
10. Wilson, A. G., Symons, J. A., McDowell, T. L., di Giovine, F. S. and Duff, G. W. (1994) Effects of a Tumour Necrosis Factor (TNF ) promoter base transition on transcriptional activity. *Br. J. Rheumatol.* 33, 89 (abs).
11. Hill, M. R. and Cookson, W. O. C. M. (1996). A new variant of the β subunit of the high-affinity receptor for Immunoglobulin E (FcεRI-β E237G): Associations of measures of atopy and bronchial hyper-responsiveness. *Hu. Mol. Gen.* 6, 959–962.
12. Nedospsov, S. A. et al (1991). Numerous TNF/ lymphotoxin alleles tagged by two closely linked microsatellites in the upstream region of the lymphotoxin (TNFβ) gene. *J. Immunol.* 147, 1053–1059.
13. Udalova, I. A. et al (1993). Highly informative typing of the human TNF locus using six adjacent polymorphic markers. *Genomics* 16, 180–186.
14. McGuire, W. et al (1994). Variation in the TNFα promoter region associated with susceptibility to cerebral malaria. *Nature* 371, 508–510.
15. Brinkman, B. M. N. et al (1996). Relevance of the tumour necrosis alpha (TNFα) −308 promoter polymorphism in TNFα gene regulation *J. Inflammation* 46, 32–41.
16. Stuber, F. et al (1996). −308 tumour necrosis factor (TNF) polymorphism is not associated with survival in severe sepsis and is unrelated to lipopolysaccharide inducibility of the human TNF promoter. *J. Inflammation* 46, 42–50.
17. Moffatt, M. et al (1994). Genetic linkage of T-cell receptor α/δ complex to specific IgE responses. *Lancet* 343 1597–1600.
18. Eigler, A., Sinha, B., Hartmann, G. and Endres S. (1997). Taming TNF: strategies to restrain this proinflammatory cytosine. *Immunology Today,* 18: 487–492.

The following Examples will now illustrate in more detail, the method according to the present invention. However, the Examples should not be construed to limit the spirit and scope of the claims.

EXAMPLES

Description of Laboratory Testing

The role of LT NcoI, and TNF −308 alleles in asthmatic and normal subjects was investigated. 413 subjects from 88 nuclear families were identified from an Australian random population as described in detail previously (11), and 410 British individuals were from 66 nuclear and 5 extended pedigrees ascertained through members with asthma or rhinitis, as previously described (17).
Methods In Australian subjects a respiratory questionnaire, based on the ATS questionnaire, was administered. "Asthma" was defined as a positive answer to the questions. "Have you ever had an attack of asthma?" and "If yes, has this happened on more than one occasion?". "Wheeze" was a positive answer to the questions "Has your chest ever sounded wheezing or whistling?" and "If yes, has this happened on more than one occasion?". Shortness of breath was a positive answer to the question "Have you ever had an attack of shortness of breath that came on when you were not exercising and without obvious cause? and "If yes, has this happened on more than one occasion?". Attacks of shortness of breath with wheezing was a positive answer to the question "Have you ever had attacks of shortness of breath with wheezing?". The use of inhaled bronchodilators and steroids was recorded.

Bronchial responsiveness to methacholine was measured by the rapid method of Yan Salome and Woolcock (Thorax 1983; 38: 760–5): the maximum dose administered was 12 μmol. The slope of the dose-response curve was calculated as (pre-dose forced expiratory volume in one second (FEV1)−last FEV1)÷the final dose of methacholine. A constant (0.01) was added to all values so that a slope of 0 could be log-transformed. Log-transformation gave a normally distributed variable. In British subjects asthma was physician-diagnosed asthma. Wheeze and bronchial responsiveness was not researched in British subjects. Blood was taken by venipuncture for IgE assays and DNA studies. The total serum IgE was determined (Pharmacia CAP system FEIA, Sweden).

PCR of the LTα NcoI polymorphism was carried out using the primers 5'-CCGTGCTTCGTGCTTTGGACTA-3' (SEQ. ID NO:1) and 5'-AGAGCTGGTGGGGACATGTCTG-3'(SEQ. ID NO:2) generating a 750 bp product. 200 ng of genomic DNA extracted from venous blood was added to a 15 μl reaction mixture containing 0.5 μM of each primer with 200 μM of each dNTP, 67 mM Tris-HCl, 16 mM $(NH_4)_2SO_4$, 0.01% Tween-20, 1 mM $MgCl_2$ and 0.45U Taq DNA polymerase. Amplification conditions were 95° C. for 6 min followed by 30 cycles of 95° C. for 1 min, 64° C. for 1 min, 72° C. for 1 min. A final extension of 72° C. for 5 min was included. Following amplification, 5 μl of PCR product was digested with 5U of NcoI (New England Biolabs) at 37° C. for 1 hour. Resultant products were analyzed on 2% agarose gels. LT NcoI allele 1 was identified by 250 and 500 bp fragments, and allele 2 by a single 750 bp band.

Typing of the TNF −308 polymorphism was by non-radioactive sequence specific oligonucleotide (SSO) probing of PCR products as described previously (14). The probe used for TNF −308 allele 1 was 5'-AGGGGCATGGGGACGGG-3'(SEQ. ID NO:3). The probe used for TNF −308 allele 2 was 5'-AGGGGCATGAGGACGGG -3'(SEQ. ID NO:4) (14). 200 ng of genomic DNA was used in each PCR reaction with a final $MgCl_2$ concentration of 1 mM. 1.5U of Taq DNA polymerase were added prior to amplification with the initial denaturation of 95° C. being decreased to 5 min. Amplification failed in 16 subjects. After dotting of denatured PCR products, filters were baked at 120° C. for 25 min prior to hybridisation with labelled probes. Temperature of the 3M TMAC stringent wash was 62° C. for both probes. Controls of known genotype were included on each filter. Accuracy of the method was confirmed by modified direct DNA sequencing of two TNF −308 allele 1 homozygotes, two TNF −308 allele 2 homozygotes and two heterozygotes from each data set. The sequencing primer was 5'-CAAACACAGGCCTCAGGACTC-3'(SEQ. ID NO:5).

HLA-DRB1 genotypes for British subjects had previously been determined by SSO probing of PCR products. For the Australian subjects, HLA-DRB1 typing was carried out using the same methodology but using probes end-labelled with digoxigenin-ddUTP (Boehringer Mannheim). The HLA-DRB1 types examined included HLADRB1*01-*14. Subtypes were recognised for HLA-DRB1*05 (HLA-DRB1*11 and HLA-DRB1*12) and for HLA-DRB1*06 (HLA-DRB1*13 and HLA-DRB1*14).

Genotypes were checked independently by two individuals, without prior knowledge of the phenotype.

Associations with the various phenotypes were sought by is contingency table analysis (SPSS 4.1 for VAX/VMS, SPSS Inc., USA, and STATXACT 2.11, Cytel Corp, USA). Examination of pedigrees allowed haplotypes on individual chromosomes to be constructed for the three loci. Associations between haplotypes and asthma were tested by Fisher's exact test (STATXACT 2.11). Alleles on unambiguous haplotypes were tested for linkage disequilibrium by analysis of contingency tables.

Results

TABLE 1

Tumour Necrosis Factor polymorphism and Asthma in two populations a) LTα NcoI polymorphism

| | LTα NcoI Genotypes | | | | |
|---|---|---|---|---|---|
| | 1,1 | 1,2 | 2,2 | $x^2$ | p |
| Australian | | | | | |
| Asthma | | | | | |
| no | 34 (11%) | 133 (43%) | 142 (46%) | 10.5 | 0.003 |
| yes | 19 (22%) | 42 (48%) | 26 (30%) | | |
| British | | | | | |
| Asthma | | | | | |
| no | 29 (15%) | 95 (50%) | 66 (35%) | 5.75 | 0.06 |
| yes | 39 (24%) | 84 (51%) | 42 (25%) | | | b) TNF-308 promoter polymorphism

| | TNF-308 Genotypes | | | | |
|---|---|---|---|---|---|
| | 1,1 | 1,2 | 2,2 | $x^2$ | p |
| Australian | | | | | |
| Asthma | | | | | |
| no | 208 (68%) | 88 (29%) | 11 (4%) | 11.5 | 0.003 |
| yes | 43 (50%) | 36 (41%) | 8 (9%) | | |
| British | | | | | |
| Asthma | | | | | |
| no | 122 (65%) | 63 (33%) | 4 (2%) | 11.6 | 0.003 |
| yes | 83 (50%) | 68 (41%) | 14 (9%) | | |

No HLA associations with asthma were found in either population (data not shown), in particular with HLA-DRB1*03, which is identified with increased TNF secretion in Australian subjects, homozygotes and heterozygotes for LTα NcoI allele 1 showed a significant increase in the prevalence of asthma (p=0.003) (Table 1a), consistent with the increased secretion of TNF recognised with this allele. LTα NcoI alleles showed only marginal association with asthma in the British subjects (p=0.06) (Table 1a).

In the case of the promoter variant TNF −308, a strong relationship with asthma was seen in both sets of subjects (Table 1b), and in both populations combined ($x^2$=24.2, p=0.0000). Asthma was increased in subjects carrying TNF −308 allele 2, again consistent with the hypothesis of increased TNF secretion predisposing to the disease.

TABLE 2

Association of LT NcoI/TNF-308 haplotypes and asthma

| | Haplotypes | | | | | |
|---|---|---|---|---|---|---|
| | LT NcoI*1/ TNF-308*1 | LT NcoI*1/ TNF-308*2 | LT NcoI*2/ TNF-308*1 | LT NcoI*2/ TNF-308*2 | Fisher's Statistic | p |
| Asthma | | | | | | |
| no | 94 (17%) | 90 (16%) | 378 (66%) | 8 (1%) | 15.2 | 0.0013 |
| yes | 28 (17%) | 48 (29%) | 92 (56%) | 0 | | |

For Australian subjects haplotypes were constructed. 744 individual haplotypes could be assigned unambiguously by inspection of the family data. LTα NcoI*1 was in strong linkage disequilibrium with TNF −308*2 (Odds rato 67.0, 95% Confidence Interval 32.0–140.2, p<0.0001). The LTα NcoI*1/TNF −308*2 haplotype was in strong disequilibrium with HLA-DRB1*03 (OR 29.1, 95% Cl 17.9–47.3, p=0.0000), as previously recognised. 60% of the haplotypes containing LTα NcoI*1/TNF −308*2 were HLA-DRB1*03 positive, compared with 5% of other LTα NcoI*/TNF −308* haplotypes. The LT NcoI*1/TNF −308*1 haplotype was in disequilibrium with HLA-DRB1*04 (OR 2.2, 95%Cl 1.4–3.3, p=0.0003) with 30% of the LTα NcoI*1/TNF −308*1 haplotypes being HLA-DRB1*04 positive, compared to 16% of other haplotypes.

An excess of asthma was exclusively associated with the LTα NcoI*1/TNF −308*2 haplotype (Table 4), so that it was not possible to differentiate between the effects of LTα NcoI*1 and TNF −308*2 alleles. Extension of the LTα NcoI*1/TNF −308*2 haplotype by inclusion of the HLA-DR locus found that the HLA-DRB1*03/LTα NcoI*1/TNF −308*2 haplotype did not show an excess of asthma over other haplotypes containing LTα NcoI*1/TNF −308*2, confirming the association with asthma to be independent of HLA-DR genotypes.

The $\log_e$ IgE did not show association with LTα NcoI or TNF −308 genotypes by analysis of variance, indicating the association of the TNF polymorphisms with asthma to be independent of atopy.

The study was extended to look at the remaining subjects of the Australian population, giving a final total of 1000 subjects from 230 families. Genotyping and statistical analysis was as already described. The TNF −308*2 allele was associated with asthma diagnosed in various ways, and with the objective measures of airway hyper-responsiveness. Results are summarised in Tables 3 and 4:

TABLE 3

| | TNF-308* | | Odds Ratio |
|---|---|---|---|
| | 1 | 2 | (95% Confidence Interval, P) |
| Attack of asthma on more than one occasion | | | |
| No | 1319 | 295 | 1.34 (1.02–1.77, p = 0.034) |
| Yes | 272 | 82 | |
| Attack of asthma in the last month | | | |
| No | 1424 | 326 | 1.59 (1.04–2.42, p = 0.030) |
| Yes | 88 | 32 | |

TABLE 3-continued

| | TNF-308* | | Odds Ratio |
|---|---|---|---|
| | 1 | 2 | (95% Confidence Interval, P) |
| Attack of shortness of breath with wheezing | | | |
| No | 1274 | 280 | 1.39 (1.07–1.81, p = 0.014) |
| Yes | 311 | 95 | |
| Doctor diagnosed asthma | | | |
| No | 1261 | 275 | 1.31 (1.00–1.72, p = 0.047) |
| Yes | 311 | 89 | |
| Wheeze on more than one occasion | | | |
| No | 1049 | 229 | 1.21 (0.96–1.53, p = 0.10) |
| Yes | 536 | 142 | |
| Current inhaled bronchodilator use | | | |
| No | 1440 | 322 | 1.55 (1.11–2.14, p = 0.0086) |
| Yes | 162 | 56 | |
| Current inhaled or oral steroid use | | | |
| No | 1541 | 353 | 1.79 (1.11–2.89, p = 0.016) |
| Yes | 61 | 25 | |

TABLE 4

| | TNF-308* | n | Mean (SEM) | t | p |
|---|---|---|---|---|---|
| Total Serum IgE | 1 | 1577 | 3.825 (0.042)* | −1.74 | 0.082 |
| | 2 | 375 | 3.991 (0.085)* | | |
| Bronchial Responsiveness (In Slope) | 1 | 1599 | −3.726 (0.048) | −2.18 | 0.029 |
| | 2 | 375 | −3.485 (0.102) | | |

These results demonstrate that genetic polymorphism in the tumour necrosis factor alpha gene is a predictor of asthma. Furthermore, the TNF −308*2 polymorphism is predictive of bronchodilator and inhaled or oral steroid usage in the population.

Strong associations were seen to current inhaled bronchodilator use (p=0.0086) and current inhaled or oral steroid use (p=0.016). This observation is of particular relevance because of substantial interest in therapeutic strategies targeting TNF, A number of anti-TNF reagents already exist which act at one of three levels: either inhibiting TNF synthesis, TNF processing or TNF effects (18).

Investigations into the application of anti-TNF therapeutic strategies have already shown promising results for diseases such as rheumatoid arthritis, Crohn's disease and septic shock.

Genetic associations between TNF polymorphisms and asthma phenotypes and medication usage therefore provide useful diagnostic tools. Stratification of individuals by genotype will allow prediction of clinical course of the disease (eg. severe versus mild). Genotype information may be required for optimal individual treatment by compounds acting on TNF-associated pathways.

What is claimed is:

1. A method for diagnosing an individual with asthma or an individual with a predisposition to asthma, said method comprising detecting in the individual the presence of an unusual variant form of at least one polymorphic sequence located in the regulatory regions for the TNFα and LTα genes in the TNFα/LTα locus of the MHC region of chromosome 6p, wherein the unusual variant form is selected from the group consisting of allele 1 of the NcoI polymorphism in the LTα gene and allele 2 of the TNF promoter polymorphism at position −308, said unusual variant form being associated with an increased secretion of TNF, and the presence of said unusual variant form being indicative of an individual with asthma or an individual with a predisposition to asthma.

2. The method according to claim 1, wherein the unusual variant form has at least two polymorphisms, one being allele 1 of the NcoI polymorphism in the LTα gene and the other being allele 2 of the TNF promoter polymorphism at position −308.

3. The method according to claim 1, wherein the detection step comprises performing a nucleic acid amplification to produce an amplified polymorphic sequence.

4. The method according to claim 3, wherein the detection step further comprises contacting the amplified polymorphic sequence with an endonuclease which only specifically digests the unusual variant form of the polymorphism and not any other form of the polymorphism, to indicate the presence or absence of the unusual variant form.

5. The method according to claim 3, wherein the detection step further comprises probing the amplified polymorphic sequence with an oligonucleotide probe which (1) specifically hybridizes to the unusual variant form of the polymorphism or (2) specifically hybridizes to any other form of the polymorphism, to identify the presence or absence of the unusual variant form.

6. A method for the prognosis of asthma in an individual, said method comprising detecting in the individual the presence of an unusual variant form of at least one polymorphic sequence located in the regulatory regions for the TNFα and LTα genes in the TNFα/LTα locus of the MHC region of chromosome 6p, wherein the unusual variant form is selected from the group consisting of allele 1 of the NcoI polymorphism in the LTα gene and allele 2 of the TNF promoter polymorphism at position −308, said unusual variant form being associated with an increased secretion of TNF, and the presence of said unusual variant form being indicative of the prognosis of asthma in the individual.

7. The method according to claim 6, wherein the unusual variant form has at least two polymorphisms, one being allele 1 of the NcoI polymorphism in the LTα gene and the other being allele 2 of the TNF promoter polymorphism at position −308.

8. The method according to claim 6, wherein the detection step comprises performing a nucleic acid amplification to produce an amplified polymorphic sequence.

9. The method according to claim 8, wherein the detection step further comprises contacting the amplified polymorphic sequence with an endonuclease which only specifically digests the unusual variant form of the polymorphism and not any other form of the polymorphism, to indicate the presence or absence of the unusual variant form.

10. The method according to claim 8, wherein the detection step further comprises probing the amplified polymorphic sequence with an oligonucleotide probe which (1) specifically hybridizes to the unusual variant form of the polymorphism or (2) specifically hybridizes to any other form of the polymorphism, to identify the presence or absence of the unusual variant form.

11. A method of testing an asthmatic individual's suitability for treatment with anti-TNF therapy, said method comprising detecting in the individual the presence of an unusual variant form of at least one polymorphic sequence located in the regulatory regions for the TNFα and LTα genes in the TNFα/LTα locus of the MHC region of chromosome 6p, wherein the unusual variant form is selected from the group consisting of allele 1 of the NcoI polymorphism in the LTα gene and allele 2 of the TNF promoter polymorphism at position −308, said unusual variant form being associated with an increased secretion of TNF, and the presence of said unusual variant form being indicative of the asthmatic individual's suitability for treatment with anti-TNF therapy.

12. The method according to claim 11, wherein the unusual variant form has at least two polymorphisms, one being allele 1 of the NcoI polymorphism in the LTα gene and the other being allele 2 of the TNF promoter polymorphism at position −308.

13. The method according to claim 11, wherein the detection step comprises performing a nucleic acid amplification to produce an amplified polymorphic sequence.

14. The method according to claim 13, wherein the detection step further comprises contacting the amplified polymorphic sequence with an endonuclease which only specifically digests the unusual variant form of the polymorphism and not any other form of the polymorphism, to indicate the presence or absence of the unusual variant form.

15. The method according to claim 13, wherein the detection step further comprises probing the amplified polymorphic sequence with an oligonucleotide probe which (1) specifically hybridizes to the unusual variant form of the polymorphism or (2) specifically hybridizes to any other form of the polymorphism, to identify the presence or absence of the unusual variant form.

* * * * *

SEQUENCE LISTING

<160> NUMBER OF SEQ ID NOS: 5

<210> SEQ ID NO 1
<211> LENGTH: 22
<212> TYPE: DNA
<213> ORGANISM: PRIMER

<400> SEQUENCE: 1
ccgtgcttcg tgctttggac ta                    22

<210> SEQ ID NO 2
<211> LENGTH: 22
<212> TYPE: DNA
<213> ORGANISM: PRIMER

<400> SEQUENCE: 2
agagctggtg gggacatgtc tg                    22

<210> SEQ ID NO 3
<211> LENGTH: 17
<212> TYPE: DNA
<213> ORGANISM: PROBE

<400> SEQUENCE: 3
aggggcatgg ggacggg                          17

<210> SEQ ID NO 4
<211> LENGTH: 17
<212> TYPE: DNA
<213> ORGANISM: PROBE

-continued

```
<400> SEQUENCE: 4 agggcatga ggacggg                                              17

<210> SEQ ID NO 5
<211> LENGTH: 21
<212> TYPE: DNA
<213> ORGANISM: PRIMER

<400> SEQUENCE: 5
caaacacagg cctcaggact c                                        21
```